(12) United States Patent
Muzzio et al.

(10) Patent No.: US 7,571,871 B2
(45) Date of Patent: Aug. 11, 2009

(54) UNIFORM SHEAR APPLICATION SYSTEM AND METHODS RELATING THERETO

(75) Inventors: Fernando J. Muzzio, Sparta, NJ (US); Lev Tsygan, Brooklyn, NY (US); Semen Dukler, Brooklyn, NY (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 11/267,039

(22) Filed: Nov. 4, 2005

(65) Prior Publication Data

US 2007/0113673 A1 May 24, 2007

(51) Int. Cl.
B02C 17/00 (2006.01)
B02C 23/02 (2006.01)

(52) U.S. Cl. .................. 241/172; 241/258; 241/262

(58) Field of Classification Search .............. 241/257.1, 241/258, 262, 248, 36, 172
See application file for complete search history.

(56) References Cited

U.S. PATENT DOCUMENTS

| | | | | |
|---|---|---|---|---|
| 4,504 A | * | 5/1846 | Webster | 165/46 |
| 220,626 A | * | 10/1879 | Leavitt | 241/157 |
| 777,228 A | * | 12/1904 | Upton | 241/79.3 |
| 1,324,389 A | * | 12/1919 | Ekola | 241/246 |
| 2,838,981 A | * | 6/1958 | Dent | 241/161 |
| 3,305,180 A | * | 2/1967 | Tomlinson | 241/14 |
| 3,420,456 A | * | 1/1969 | Ugalde et al. | 241/46.04 |
| 3,455,235 A | * | 7/1969 | Koelsch | 100/37 |
| 4,620,673 A | * | 11/1986 | Canepa et al. | 241/69 |
| 4,848,676 A | * | 7/1989 | Stehr | 241/33 |
| 4,915,307 A | * | 4/1990 | Klimaschka et al. | 241/65 |
| 5,285,973 A | * | 2/1994 | Goforth et al. | 241/36 |
| 5,395,059 A | * | 3/1995 | Satake et al. | 241/74 |
| 5,853,132 A | * | 12/1998 | Tsuji | 241/172 |
| 6,021,969 A | * | 2/2000 | Schmitt et al. | 241/171 |
| 6,669,123 B2 | * | 12/2003 | Spyra | 241/36 |

* cited by examiner

*Primary Examiner*—Bena Miller
(74) *Attorney, Agent, or Firm*—McCarter & English, LLP

(57) ABSTRACT

Disclosed herein is a shear application system for applying substantially uniform amounts of shear throughout a powder sample. The shear application system preferably includes a cylinder assembly having an inner cylinder, a housing, an inner set of lugs, and an outer set of lugs. The inner cylinder has an external cylindrical surface and the housing has an internal cylindrical surface concentric with said external cylindrical surface. The internal and external cylindrical surfaces form an annular chamber therebetween. Each one of the lugs of the inner set extend radially outward from the external cylindrical surface, and each one of the lugs of the outer set extend radially inward from the internal cylindrical surface and are substantially uniformly spaced. The shear application system preferably includes drive means mechanically connected to the inner cylinder and control means electrically connected to the drive means.

21 Claims, 13 Drawing Sheets

UNIFORM SHEAR APPLICATION SYSTEM AND METHODS RELATING THERETO

FIELD OF THE INVENTION

The present invention relates generally to systems, methods, and devices for imparting shear to a powder sample.

BACKGROUND OF THE INVENTION

As used herein, shear refers to the sliding motion of particles relative to one another, and shear stress is the application of forces to particles resulting from said sliding motion. Total applied shear or total shear refers to the total shear applied to a sample of particles over the entire process of holding, processing, and mixing the sample of products.

Shear plays an important role in the processing of pharmaceutical blends and other powder samples, thereby effecting the performance of mixtures. It has been known that excessive amounts of shear applied to a powder sample for a significant amount of time decreases the hardness, increases capping, and decreases the dissolution of tablets formed from the powder sample. It is also known in the art that the intensity of total applied shear for direct compression cohesive blends, effects particle size and shape, the density, flowability and content uniformity of said powder, and the weight variability of tablets formed therefrom. Furthermore, it is also known that the total applied shear correlates to electrostatic charging of the powder sample, which is a safety hazard and interferes with the process of manufacturing tablets from a powder sample. However, these relationships are not easily quantified.

It would be advantageous to study the physical relationships between the shear applied to a powder sample and the properties of tablets formed therefrom. An understanding of these physical relationships could be used, for example, to advance the state of the art in tablet production. However, in spite of its significant impact, shear has not been studied systematically. Typically, varying amounts of shear have been applied (often unintentionally) in a blender and/or in a feed frame. In both of these environments, the granular flow of the powder sample is poorly understood and the intensity and uniformity of shear that is applied to the powder sample is unknown. As a result, the knowledge in the art relating to the effect shear has on tablets is typically qualitative at best. In this regard, it is further unknown in the art how the amount of shear applied to a powder sample can be controlled to produce tablets having desired properties.

What is needed in the art is technology that facilitates testing and evaluation of the relationship between the shear imparted to a powder sample and the properties of the tablets produced therefrom.

SUMMARY OF THE INVENTION

The present invention overcomes the disadvantages and shortcomings of the prior art by providing systems, methods, and devices relating to the application of substantially uniform amounts of shear throughout a powder sample.

By applying a substantially uniform amount of shear throughout a powder sample, the variance in shear throughout the powder sample is decreased. The uniformly sheared powder sample may be used as a baseline for evaluating the effects of subsequent increases and/or decreases in the amount of substantially uniform shear imparted to the sheared powder sample. The sheared powder sample can be used to evaluate the relationship between the shear applied thereto and the properties of tablets produced therefrom.

The shear application system of the present invention includes a cylinder assembly having an inner cylinder, drive means for inducing rotation of the inner cylinder, and control means for actuating the drive means. Each of the cylinder assembly, drive means, and control means are discussed in turn below.

The cylinder assembly includes an inner cylinder and a housing. The inner cylinder has an external cylindrical surface. The housing includes an outer cylinder with an internal cylindrical surface concentric with the external cylindrical surface. The internal and external cylindrical surfaces form an annular chamber therebetween. The housing also includes a cover positioned over the annular chamber and a base positioned under the annular chamber.

The cylinder assembly also includes an inner set of lugs and an outer set of lugs. Each one of the lugs of the inner set extends radially outward from the external cylindrical surface of the inner cylinder. Each one of the lugs of the outer set extends radially inward from the internal cylindrical surface of the outer cylinder. Each one of the lugs of the inner and outer sets are generally square, but may have an angled forward edge. In some embodiments, the lugs are interchangeably removable from the cylinder assembly, so as to facilitate substitution of lugs having alternative geometry.

The drive means of the shear application system preferably includes a drive motor mechanically connected to the inner cylinder for rotating the inner cylinder in the direction of rotation. The control means includes a computer system electrically connected to the drive means for actuation thereof. The control means is operative to input a user-selected value representative of a desired angular velocity for rotation of the inner cylinder and is further operative to variably actuate the drive means in accordance with the user-selected value. The shear application system may be characterized as a turn-key data acquisition system.

BRIEF DESCRIPTION OF THE DRAWINGS

For a more complete understanding of the present invention, reference is made to the following detailed description of exemplary embodiments considered in conjunction with the accompanying drawings, in which.

DETAILED DESCRIPTION OF THE INVENTION

Figure 1:
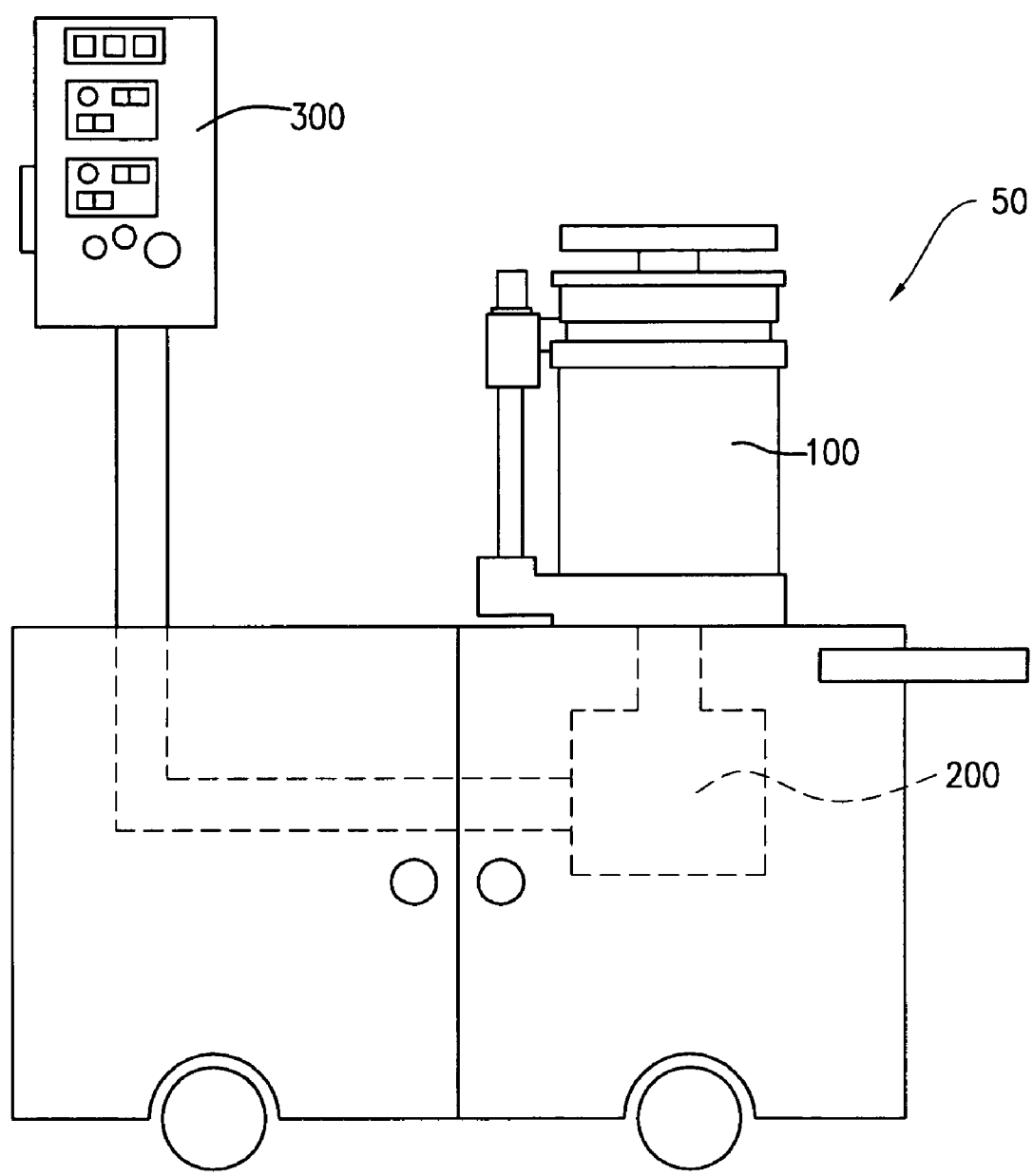
FIG. 1 is a schematic diagram showing an embodiment of a shear application system having a cylinder assembly, drive means, and control means.

With reference to FIG. 1, a shear application system 50 constructed in accordance with the present invention is shown and described. The shear application system 50 includes a cylinder assembly 100, drive means 200, and control means 300. The cylinder assembly 100 contains an inner cylinder, discussed below, that rotates. The drive means 200 includes a drive motor mechanically connected to the inner cylinder for driving the inner cylinder. The control means 300 comprises a computer system operative to input a user selection, such as angular velocity, and variably actuate the drive means 200 in accordance with the user selection. The cylinder assembly 100, the drive means 200, and the control means 300 will each be discussed below in turn.

Figure 2:
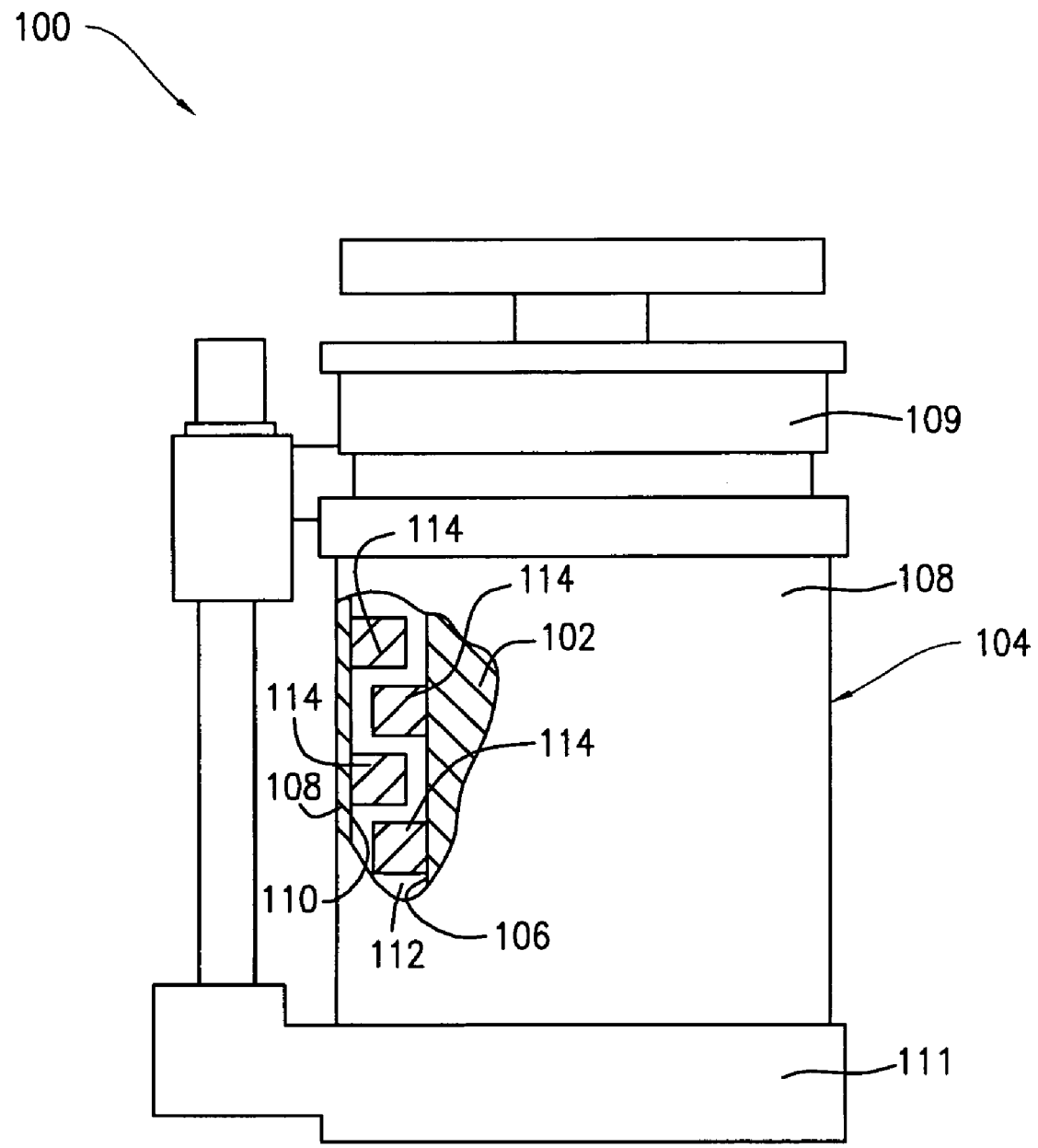
FIG. 2 is a partially broken, front perspective view showing a cylinder assembly constructed in accordance with the present invention, said cylinder assembly having an outer cylinder, a cover, a base, an inner cylinder, an inner set of lugs, and an outer set of lugs.

Referring to FIG. 2, the cylinder assembly 100 of FIG. 1 is shown to include an inner cylinder 102 and a housing 104. The inner cylinder 102 has an external surface 106 and shall be further described below with principal reference to FIGS. 3 and 4. The housing 104 includes an outer cylinder 108 having an internal cylindrical surface 110 and shall be described below with principal reference to FIGS. 5 and 6. The internal cylindrical surface 110 of the outer cylinder 108 and the external cylindrical surface 106 of the inner cylinder 102 are concentric to form an annular chamber 112 therebetween, which shall be further discussed below with principal reference to FIGS. 7 and 8.

Continuing with principal reference to FIG. 2, the housing 104 also includes a cover 109 positioned over the annular chamber 112 and a base 111 positioned under the annular chamber 112. The housing 104 may have one or more openings, inlets, outlets, valves, etc. formed therein (not shown) for the flow of a powder sample into and/or out of said annular chamber 112. The cylinder assembly 100 also includes a plurality of lugs 114 positioned in the annular chamber 112 along the internal cylindrical surface 110 and the external cylindrical surface 106.

Figure 3:
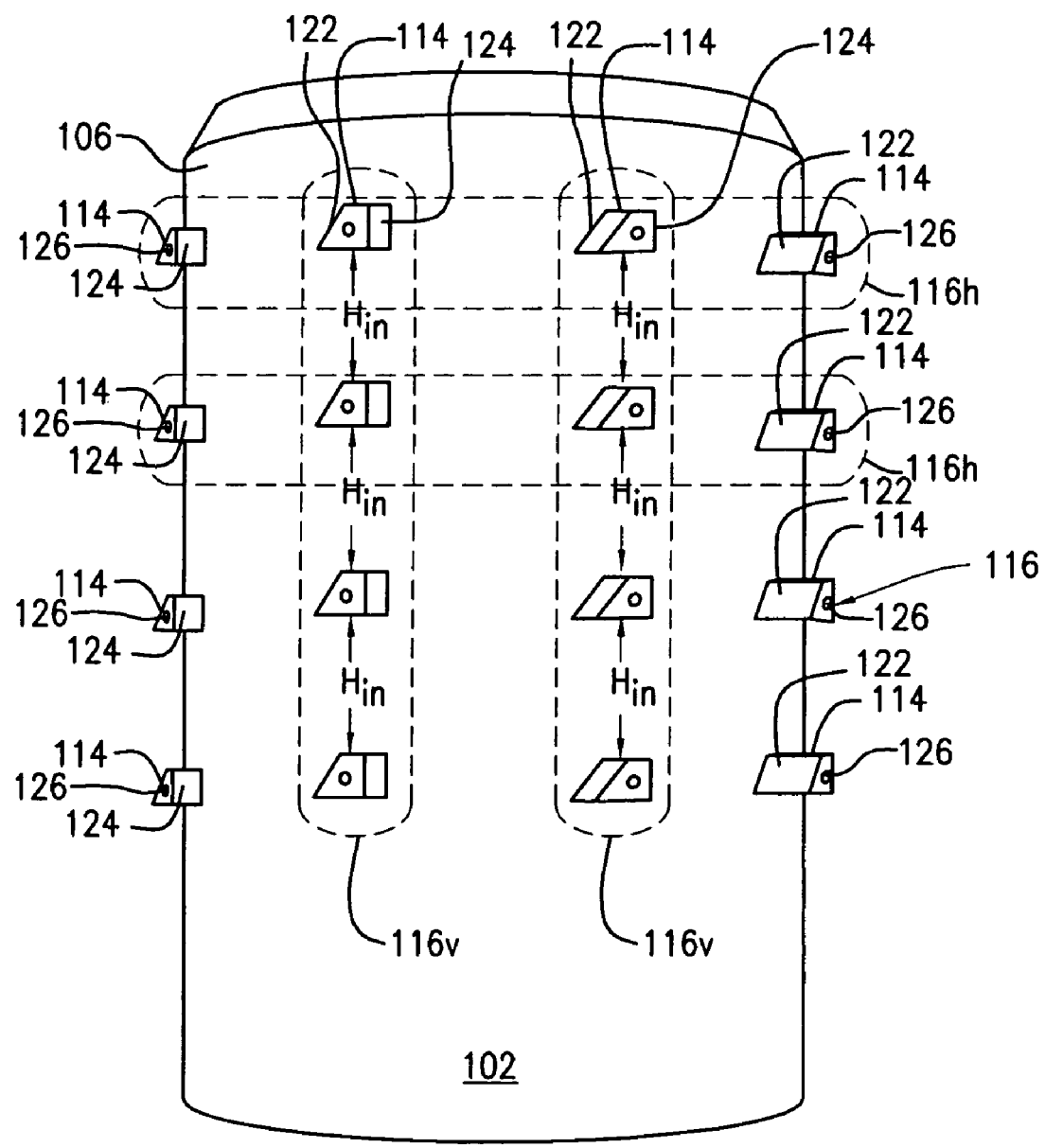
FIG. 3 is a front perspective view showing the inner cylinder and the inner set of lugs of FIG. 2.
Figure 4:
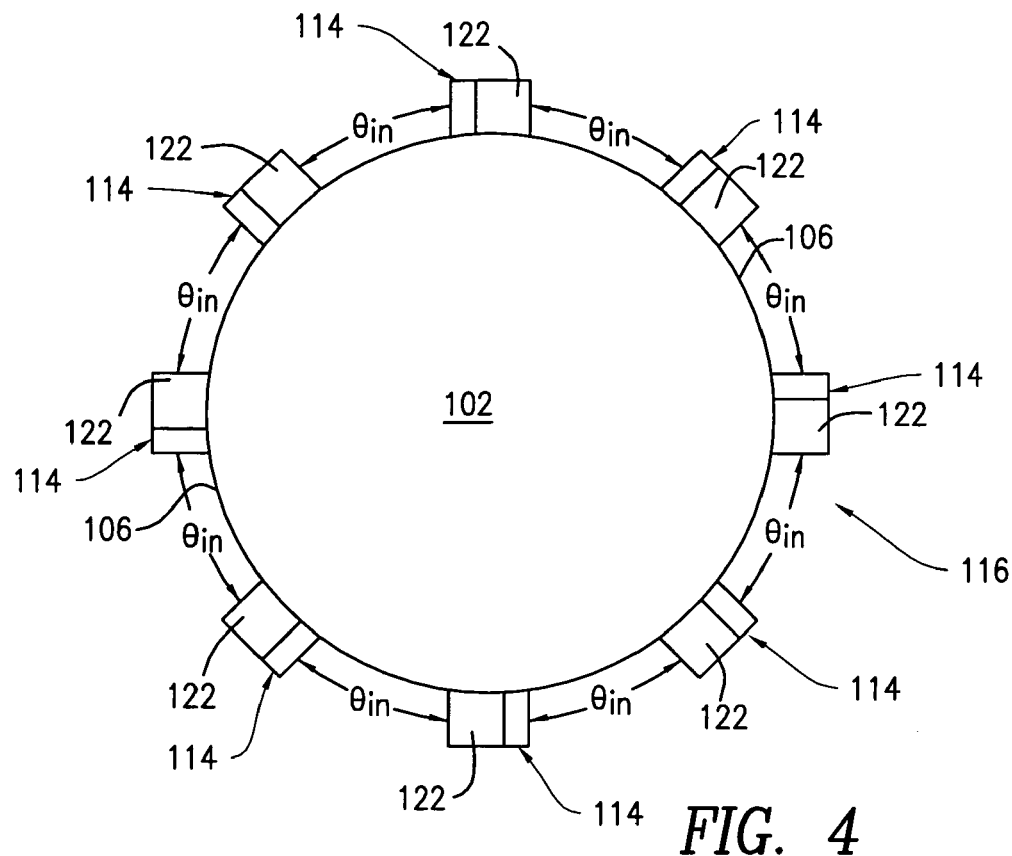
FIG. 4 is a top view showing the inner cylinder and the inner set of lugs of FIGS. 2 and 3.

Referring to FIGS. 3 and 4, the cylinder assembly 100 has an inner set 116 of lugs 114 positioned along the external cylindrical surface 106 and extending radially outward therefrom. The inner set 116 of lugs 114 comprises, for example, the sixteen (16) lugs 114 shown in FIG. 3, as well as sixteen (16) additional lugs 114 hidden from view behind the inner cylinder 102 thereof. However, the inner set 116 can include any suitable number of lugs 114. The lugs 114 of the inner set 116 form a matrix pattern about the external cylindrical surface 106 of the inner cylinder 102. In this regard, the inner set 116 of lugs 114 preferably includes a plurality of vertically-aligned inner lug subsets 116v and a plurality of horizontally-aligned inner lug subsets 116h, each lug 114 of the inner set 116 being a member of one of the vertically-aligned inner lug subsets 116v and one of the horizontally-aligned inner lug subsets 116h. It is preferred to have substantial uniformity among the lugs 114 and the spaces therebetween, so as to encourage substantial uniformity of shear.

The inner set 116 of lugs 114 includes a plurality of vertically-aligned lug subsets, such as eight (8) vertically-aligned inner lug subsets 116v of four (4) lugs 114. However, the inner set 116 of lugs 114 can include any suitable number of vertically-aligned inner lug subsets 116v and any number of lugs 114. Each lug 114 in a vertically-aligned inner lug subset 116v is preferably substantially even-spaced from each other lug 114 adjacent thereto at a distance $H_{in}$. The distance $H_{in}$ is therefore preferably substantially the same within a given vertically-aligned inner lug subset 116v and from one vertically-aligned inner lug subset 116v to another.

The inner set 116 of lugs 114 also includes a plurality of horizontally-aligned lug subsets, such as four (4) horizontally-aligned inner lug subsets 116h of eight (8) lugs 114. Each of the lugs 114 of the inner set 116 are substantially-even spaced from each other lug 114 of the inner set 116 at an angle $\theta_{in}$ about the external cylindrical surface 106. For example, in the embodiment of the present invention shown in FIGS. 3 and 4, each of the horizontally-aligned inner lug subsets 116h has eight lugs, and each of said lugs 114 are spaced apart from each other lug 114 horizontally adjacent thereto at an angle $\theta_{in}$ of $\pi/4$ radians. Each of the angle $\theta_{in}$ shown are preferably the same within a given horizontally-aligned inner lug subset 116h and from one horizontally-aligned inner lug subset 116h to another. It is not required for the angle $\theta_{in}$ to be fixed.

Figure 5:
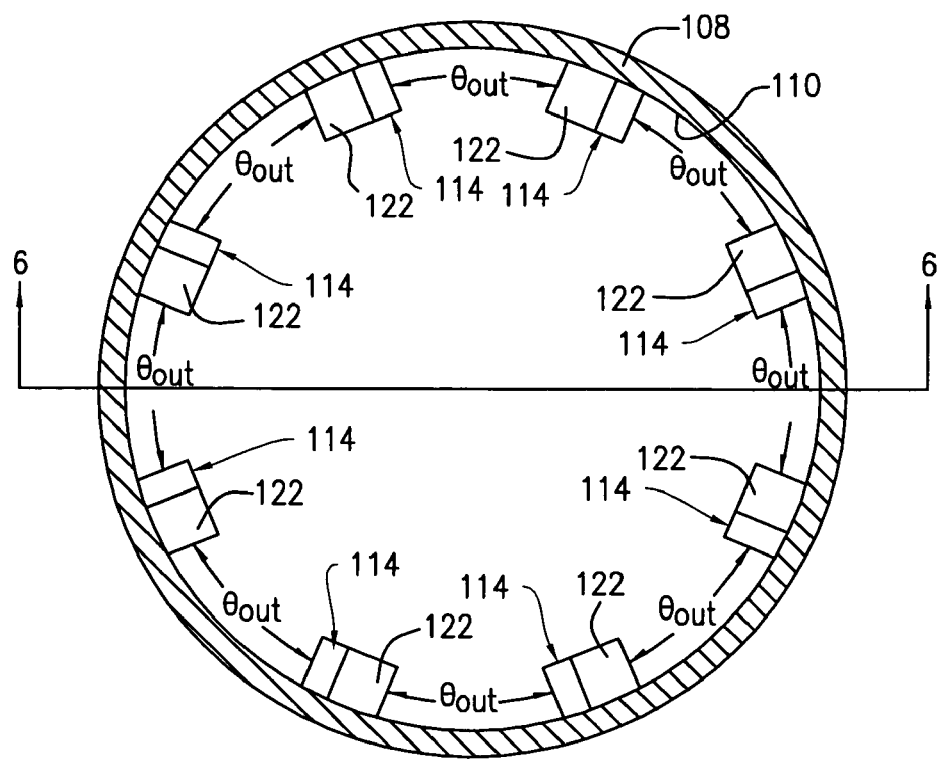
FIG. 5 is a top view showing the outer cylinder and the outer set of lugs of FIG. 2.
Figure 6:
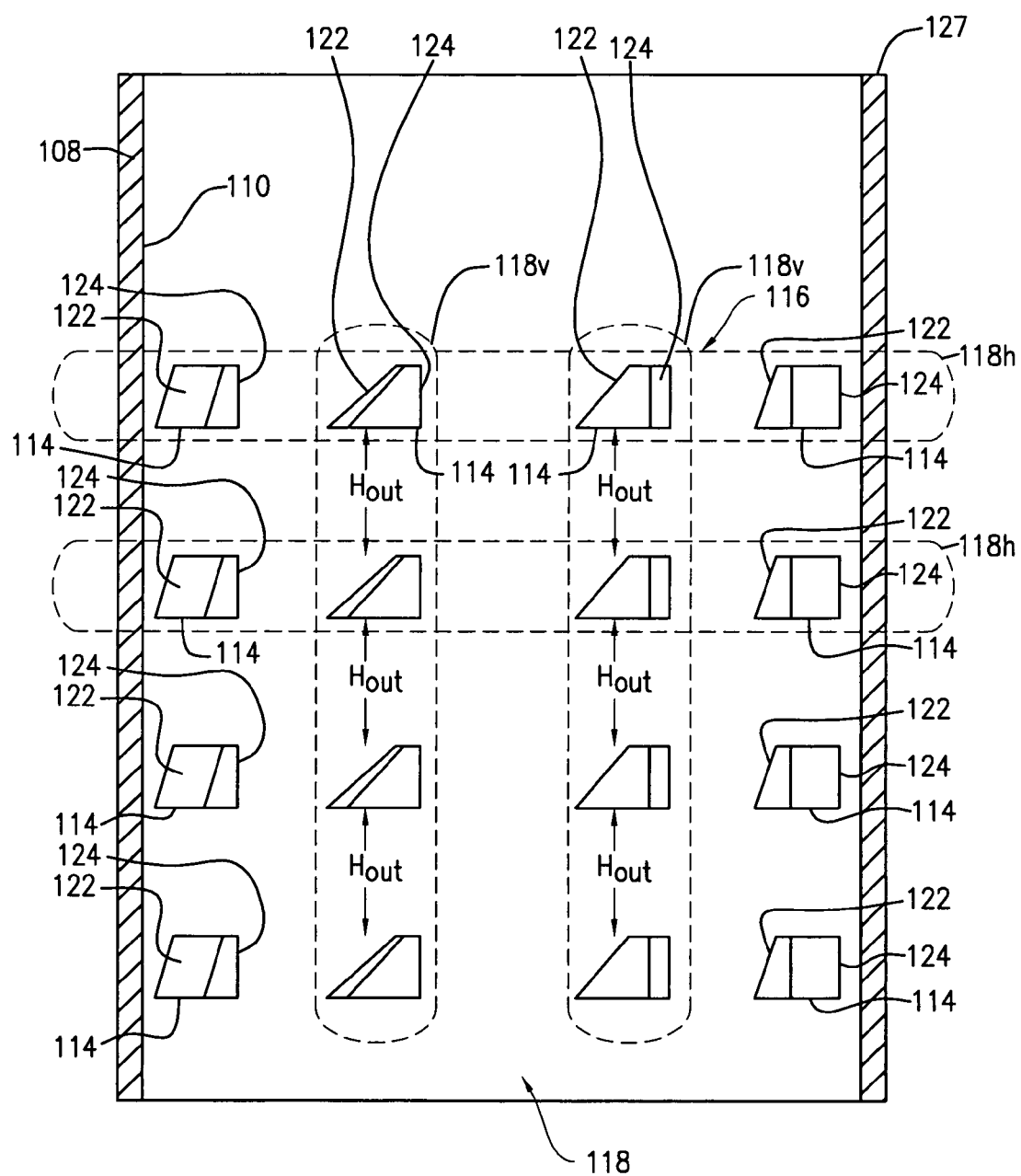
FIG. 6 is a cross-section taken along line 6-6 of FIG. 5 showing the outer cylinder and the outer set of lugs of FIGS. 2 and 5.

FIGS. 5 and 6 show the outer cylinder 108 and an outer set 118 of lugs 114 positioned along the internal cylindrical surface 110 and extending radially inward therefrom. The outer set 118 of lugs 114 comprises, for example, the sixteen (16) lugs 114 shown in FIG. 6, as well as sixteen (16) additional lugs 114, not shown, on the other half of the outer cylinder 108.

The lugs 114 of the outer set 118 form a matrix pattern about the internal cylindrical surface 110 of the outer cylinder 108. In this regard, the outer set 118 of lugs 114 preferably includes a plurality of vertically-aligned outer lug subsets 118v and a plurality of horizontally-aligned outer lug subsets 118h. Each lug 114 of said outer set 118 is a member of both a vertically-aligned outer lug subset 118v and a horizontally-aligned outer lug subset 118h.

The outer set 118 of lugs 114 includes a plurality of vertically-aligned lug subsets, such as eight (8) vertically-aligned outer lug subsets 118v having four (4) lugs 114 each. However, the outer set 118 of lugs 114 can include any suitable number of vertically-aligned outer lug subsets 118v. Each lug 114 of each vertically-aligned outer lug subset 118v is preferably substantially even-spaced from each other lug 114 adjacent thereto at a distance $H_{out}$ in said vertically-aligned outer lug subset 118v. The distance $H_{out}$ is preferably constant both within a given vertically-aligned outer lug subset 118v and from one vertically-aligned outer lug subset 118v to another. Each lug 114 in a vertically-aligned outer lug subset 118v is also coplanar with each other lug 114 in that same vertically-aligned outer lug subset 118v.

The outer set 118 of lugs 114 is shown to include four (4) horizontally-aligned outer lug subsets 118h having eight (8) lugs 114 each. Each of the lugs 114 of the outer set 118 are substantially-even spaced from each other lug 114 of the outer set 118 at an angle $\theta_{out}$ about the external cylindrical surface 106. For example, in the embodiment shown in FIGS. 5 and 6, wherein each of the horizontally-aligned outer lug subsets 118h has eight lugs 114, each of said lugs 114 are spaced apart from lugs 114 horizontally adjacent thereto an angle $\theta_{out}$ of $\pi/4$ radians. The angle $\theta_{out}$ is preferably constant both within a given horizontally-aligned outer lug subset 118h and from one horizontally-aligned outer lug subset 118h to another. It is not required for the angle $\theta_{out}$ to be fixed.

Figure 7:
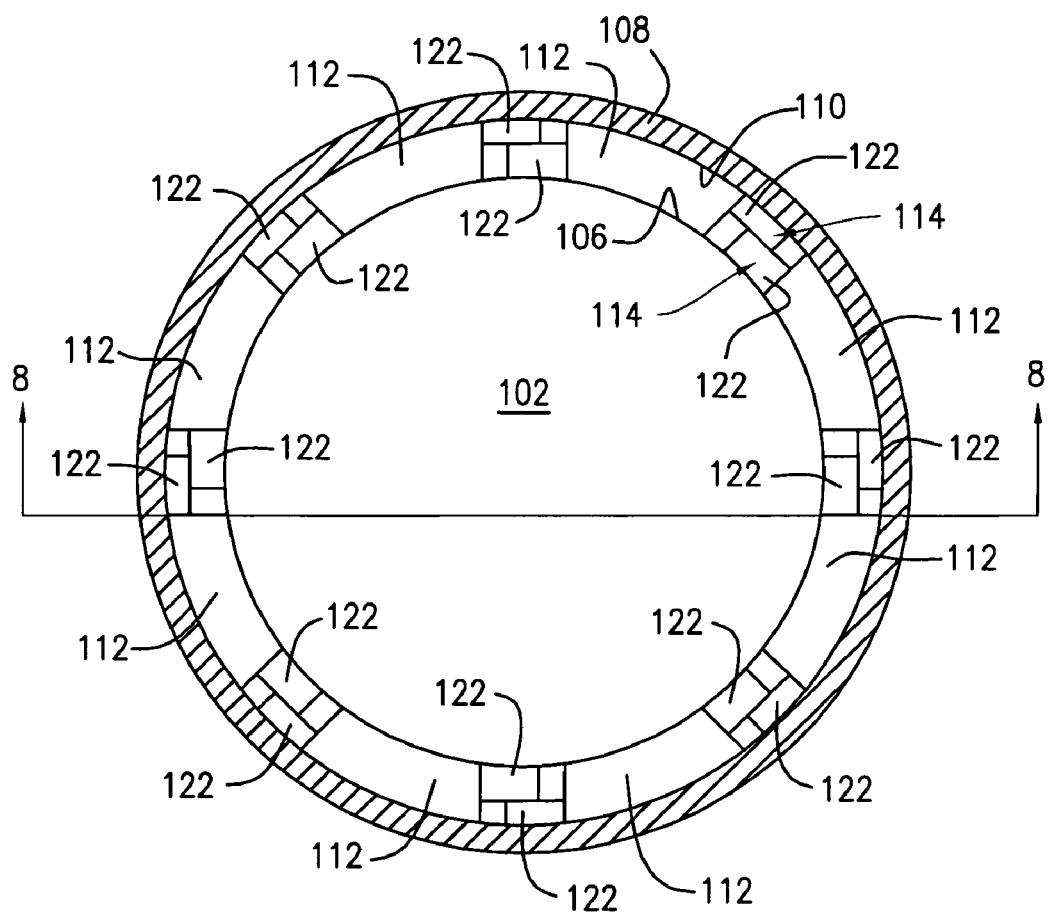
FIG. 7 is a top view showing the inner cylinder and the inner set of lugs of FIGS. 2 and 3-4, the outer cylinder and the outer set of lugs of FIGS. 2 and 5-6, and an annular chamber formed between the inner cylinder and the outer cylinder.
Figure 8:
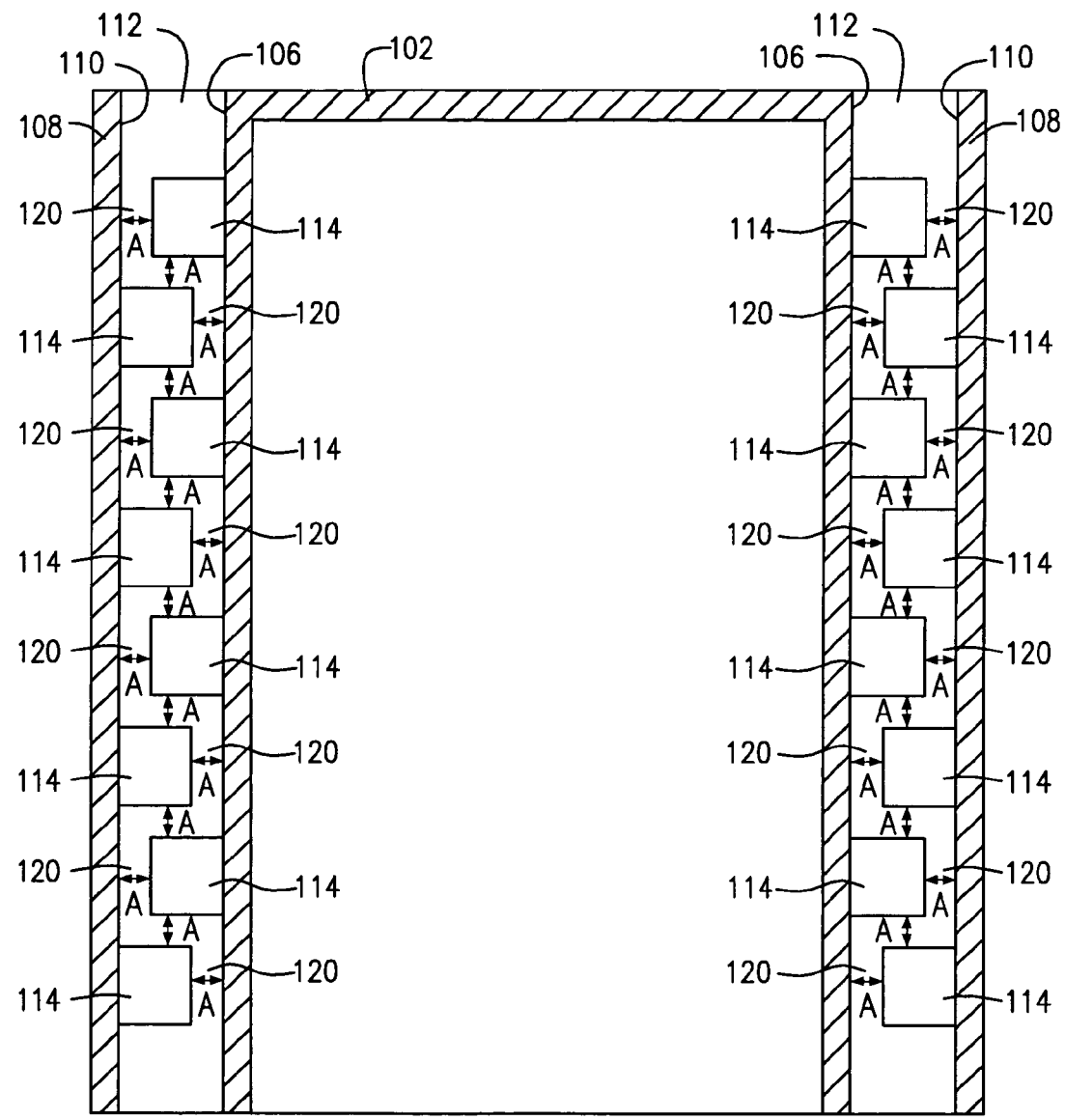
FIG. 8 is a sectional view taken along lines 8-8 of FIG. 7 showing staggering between the inner set of lugs and the outer set of lugs.

FIGS. 7 and 8 show the inner set 116 of lugs 114 extending radially outward from the external cylindrical surface 106 and the outer set 118 of lugs 114 extending radially inward from the internal cylindrical surface 110 thereof. As shown, the external cylindrical surface 106 of the inner cylinder is concentrically positioned with respect to the internal cylindrical surface 110 of the outer cylinder 108. The external cylindrical surface 106 of the inner cylinder 102 and the internal cylindrical surface 110 of the outer cylinder 108 form an annular chamber 112 therebetween. The lugs 114 of the inner set 116 and the lugs 114 of the outer set 118 extend into the annular chamber 112.

The internal cylindrical surface 110 and the lugs 114 of the inner set 116 form a first set of gaps 120 therebetween, and the external cylindrical surface 106 and the lugs 114 of the outer set 116 form a second set of gaps 120 therebetween. Each gap 120 of the first and second sets is substantially the same size as each other gap 120 of the first and second sets, which is referenced in FIG. 8 as distance A.

As shown in FIGS. 3 and 6, it is preferable that each of the lugs 114 of the inner set 116 and outer set 118 has substantially the same dimensions as each other lug 114 of the inner set 116 and outer set 118. Also, it is preferably that each lug 114 includes an inclined surface, referenced herein as an angled forward edge 122. Further, each lug 114 includes a substantially vertical surface 124 opposite the angled forward edge 122. Horizontal upper and lower surfaces and planar exterior surfaces complete the configuration of the lugs. The angled forward edge 122 of each lug 114 includes a leading edge that, with respect to those lugs 114 of the inner set 116, faces the direction in which the inner cylinder 102 is rotated by the drive means 200. As shown in FIG. 7, for example the leading edges of the angled forward edges 122 of the lugs 114 of the outer set 118 can face in a direction opposited those of inner set 116.

The lugs 114 of the inner set 116 do not contact the lugs 114 of the outer set 118 during rotation of the inner cylinder 102. In this regard, the lugs 114 of the inner set 116 are vertically staggered with respect to the lugs 114 of the outer set 118, so as not to make contact with one another. The distance $H_{in}$ between the lugs 114 of the inner set 116 is preferably about the same as the distance $H_{out}$ between the lugs of the outer set 118. The distance between each lug 114 of the inner set 116 and each lug 114 of the outer set 118 staggered adjacently therewith is preferably the same, and is preferably substantially equal to the distance A associated with each gap 120.

The lugs 114 of the inner set 116 may be interchangeably removable with the inner cylinder 102, so as to facilitate substitution of lugs having, for example, a geometry that is different from than that described above. Each lug 114 of the inner set 116 may be provided with a bore (not shown) extending therethough, and the inner cylinder 102 may be provided with a plurality of threaded openings (not shown) formed therein. In an embodiment with interchangeably removable lugs 114, the cylinder assembly 50 includes a plurality of threaded screws 126 (designated in FIG. 3), and each one of the screws 126 extend through one of the bores in the lug and into one of the threaded openings corresponding therewith to secure the lug 114 to the inner cylinder 102. As shown, the head of each screw 126 is preferably flush with respect to the planar exterior surface of the lug 114 corresponding therewith. Although not shown, it is contemplated that the lugs 114 of the outer set 118 and/or the housing 104 may also include means for interchangeably removing the lugs 114.

As stated above, the shear application system 50 also includes the drive means 200. The drive means 200 includes a drive motor positioned within a table-like structure and mechanically connected to the inner cylinder 102 for rotation thereof. The shear application system 50 also includes control means 300 for variably actuating said drive means 200. The control means 300 comprises, for example, a computer system electrically connected to the drive means 200 for control thereof. The computer system may have an input device, an output device, a display, a processor, an at least temporary memory, etc., and preferably has a Windows XP operating system stored thereon and a Pentium processor.

The shear application system 50 may also include one or more sensors (not shown) for sensing/reading attributes associated with the powder sample and/or the cylinder assembly (e.g., a torque transducer). In some embodiments of the invention, the sensors may send said attributes to the control means 300. The attributes read by the sensors may include, for example, the angular velocity of the inner cylinder 102, the angular momentum of the inner cylinder 102, and the force required to rotate the inner cylinder 102 at a desired angular velocity. Upon actuation of the drive means 200, the inner cylinder 102 rotates with respect to the outer cylinder 108, thereby causing the angled forward edges 122 of the lugs 114 to plow through the powder sample contained therein, creating a relatively uniform mixing environment which applies shear to the powder sample.

It shall be understood by one skilled in the art that the lugs may be of any size, shape, and position suitable for imparting substantially uniform amounts of shear to a powder sample in the annular chamber. It shall be further understood by one skilled in the art that the cylinder assembly may include any suitable projections extending from the external cylindrical surface 106 and/or the internal cylindrical surface 110, and that the invention is not limited so as to require the lug 114 or another particular type of a projection. In this regard, the inside surfaces of the cylinder assembly could include cylindrical surfaces, projection surfaces, and recesses, or any suitable profile, so long as the inside surfaces co-act to impart substantially uniform amounts of shear to a powder sample.

Referring to FIGS. 9-13, testing was conducted using a shear application system constructed in accordance with the invention and a one kilogram powder sample having 0-2% Magnesium Stearate (MgSt). In conducting the testing, a drive motor rotated an inner cylinder of a cylinder assembly at a constant speed so as to apply substantially uniform shear to a powder sample positioned therein. Sensors continuously read the total torque and angular velocity of the inner cylinder. The shear application system created a controlled shear environment, where the homogenization of the powder sample could be studied under carefully controlled, homogenously applied shear rates. The shear application system successfully applied known amounts of shear homogenously and at a controlled rate, making it possible to design experiments where the relationships between the measured forces, the observed flow, and the mixing phenomena would be better understood. The inner and outer lug sets achieved a substantially homogenous shear field in the powder sample flowing through the annular chamber for controlled periods, thus providing a suitable environment for investigating the effect of shear on tablet hardness, dissolution, density, and flow properties. Experiments were performed in order to examine the effect of shear and MgSt content on blend flow properties, MgSt homogeneity, bulk density, and tablet hardness, using a blend of 58-60% Fast-flo lactose, 40% Avicel 102, and 0-2% MgSt.

Figure 9:
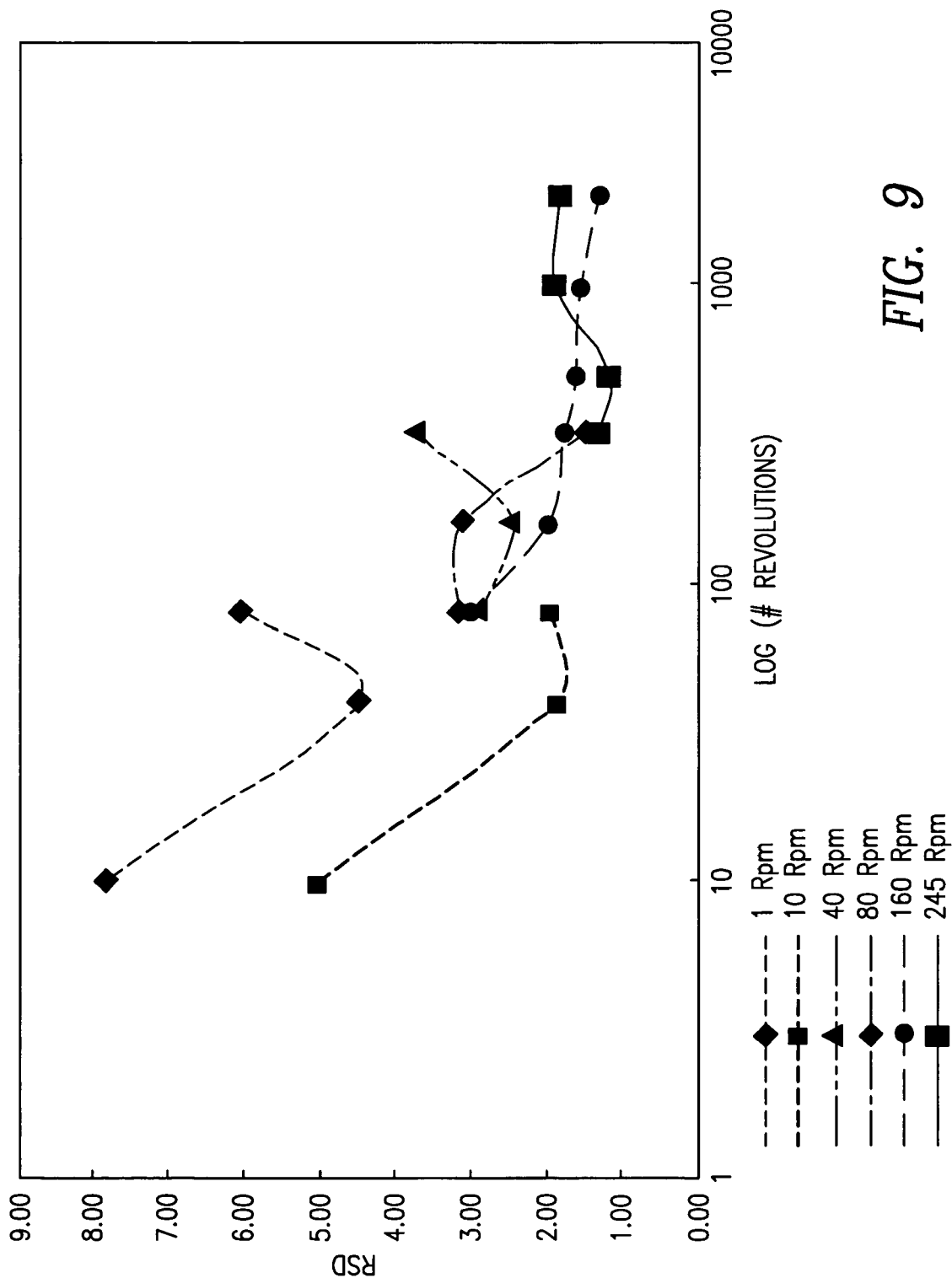
FIG. 9 is a chart showing a plurality of test results obtained by using a shear application system constructed in accordance with the invention.

With reference to FIG. 9, the blends were sheared at various rates in the range of 10 to 245 rotations per minute, which corresponds to shear rates between $1.25\ s^{-1}$ and $300\ s^{-1}$ for a total of 10 to 2000 revolutions (corresponding to 750 to 150000 total shear units), and were subsequently sampled. Bulk density, flow properties, and MgSt RSD were subsequently characterized. Moreover, selected samples were compressed under conditions simulating operations of commercial presses, and the tablets were then tested for crushing hardness.

FIG. 9 shows that the relative standard deviation (RSD) of shear throughout the sample decreases by adding more shear and then reaches a plateau. RSD of the MgSt may be substantially minimized by applying substantially uniform amounts of shear thereto. The resulting RSD of the MgSt concentration was a function of the total number of revolutions in the device. As the total shear increases, MgSt RSD decreases and then reaches a distinctive plateau, suggesting the existence of two separate regimes, one where MgSt homogeneity depends on shear, and another where a maximum degree of lubrication (or over-lubrication) has been achieved. The concentration of lubricant MgSt used was 1%.

Figure 10:
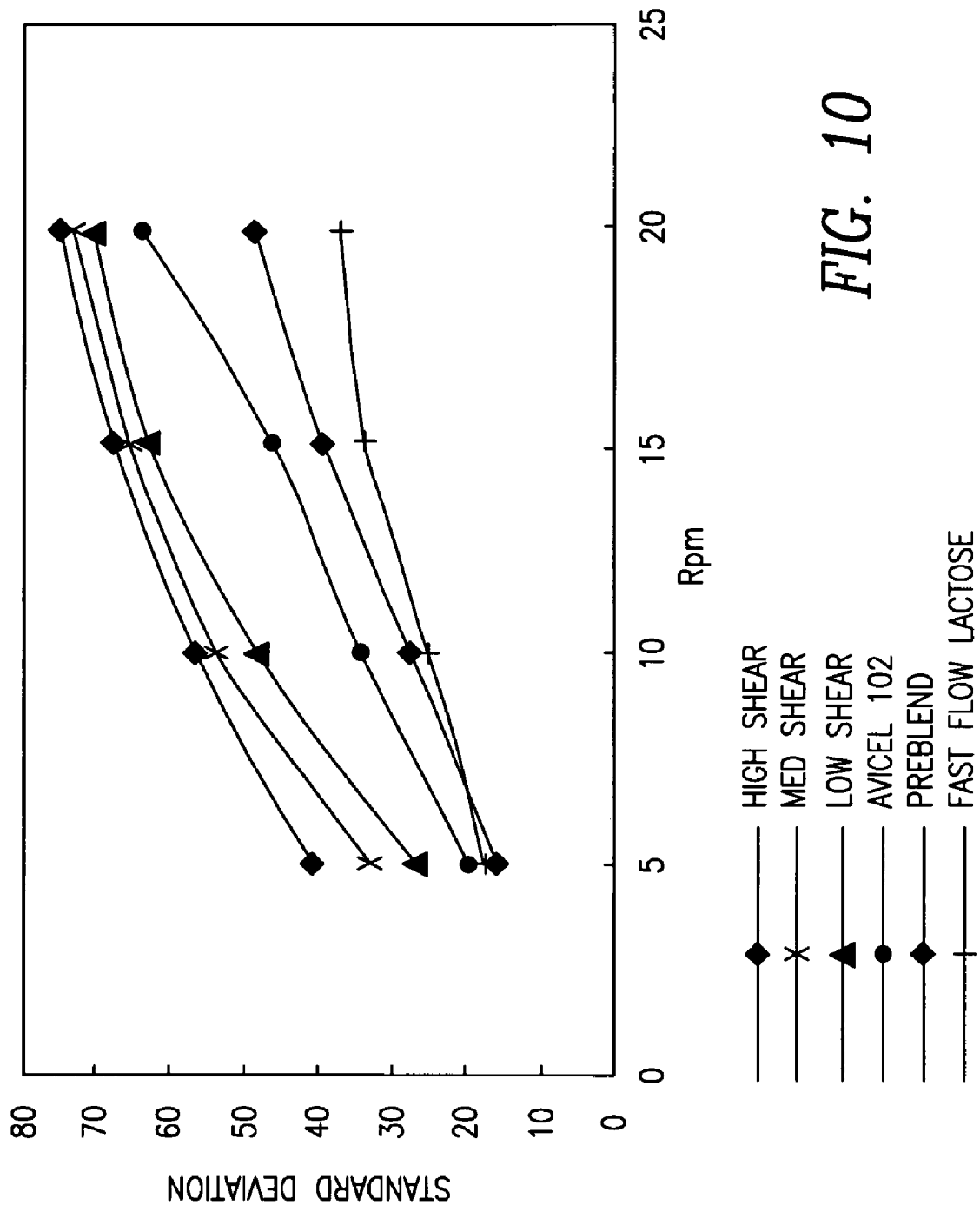
FIG. 10 is a chart showing relationships between the shear applied to a powder sample and the flowability thereof.

Referring to FIG. 10, flow properties of the powder samples were strongly affected by shear. The flow properties were studied in terms of the size of avalanches observed under dilated conditions in a gravitational displacement rheometer. Blend cohesion increased as total shear increased. FIG. 10 shows the cohesive flow properties of Avicel 102, Fast-flow lactose, a pre-blend, and a mixture (60% fast-flow lactose and 40% Avicel 102) treated with three different amounts of shear using an embodiment of the shear application system, a lower amount of shear (e.g., approximately 500 revolutions), a medium amount of shear (e.g, approximately 2000 revolutions), and a higher amount of shear (e.g., approximately 5000 revolutions). Weight variance was calculated in accordance with measurements taken with the gravitational displacement rheometer. It is observed that the powder sample with the highest shear has the highest cohesive index (as shown in the top of the curve of FIG. 10).

Figure 11:
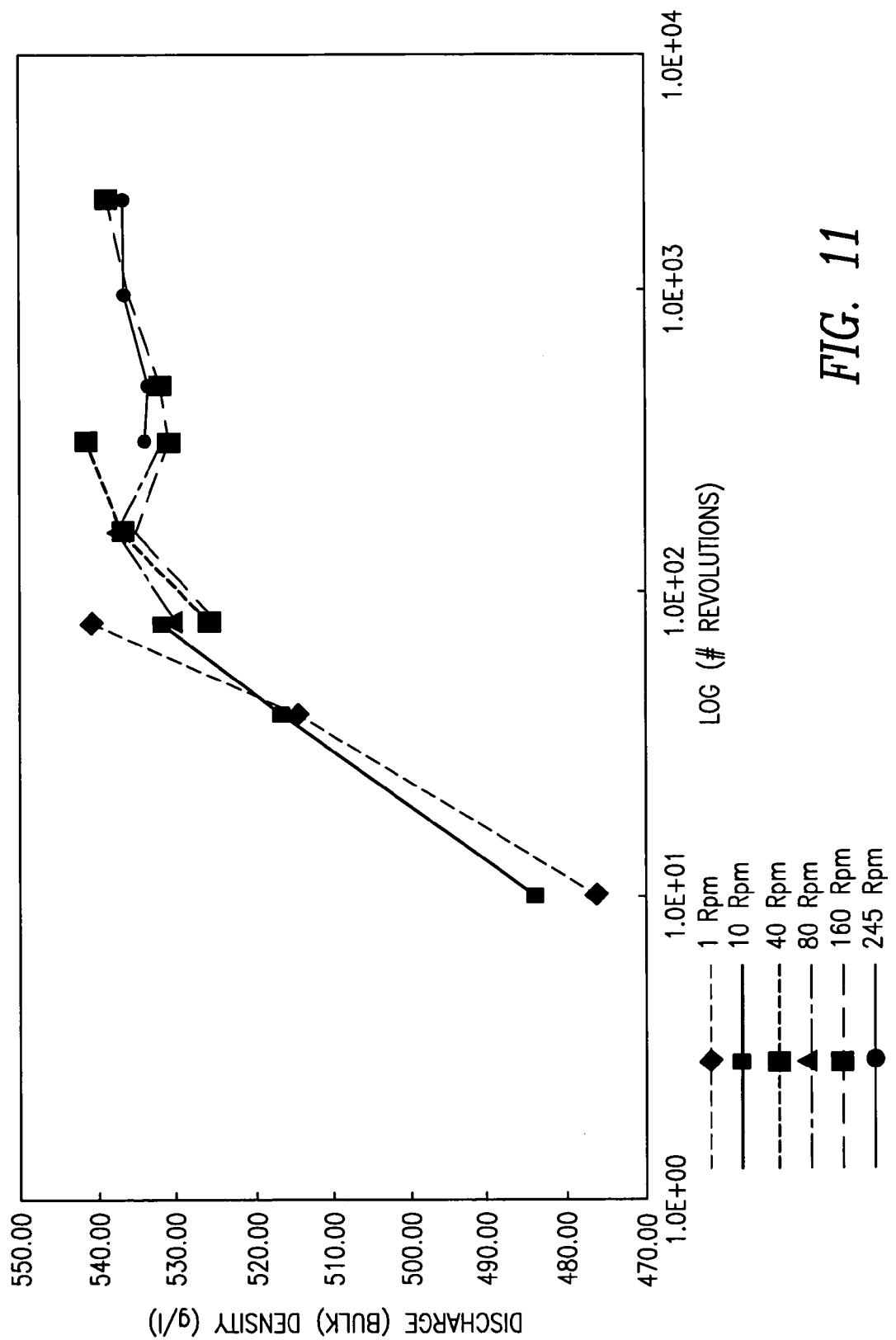
FIG. 11 is a chart showing relationships between the shear applied to a powder sample and the bulk density thereof.

With reference to FIG. 11, it was observed that bulk density, which has a strong effect on tablet weight and content uniformity, is another variable affected by the total amount of applied shear. For example, FIG. 11 shows that the bulk density of a mixture (59% Fast Flo Lactose, 40% Avicel 102 and 1% MgSt) increases and then reaches a plateau, suggesting the existence of two regimes closely related to those observed for MgSt RSD. In this test, the bulk density increased as the total shear increased and finally reached a constant value.

Figure 12:
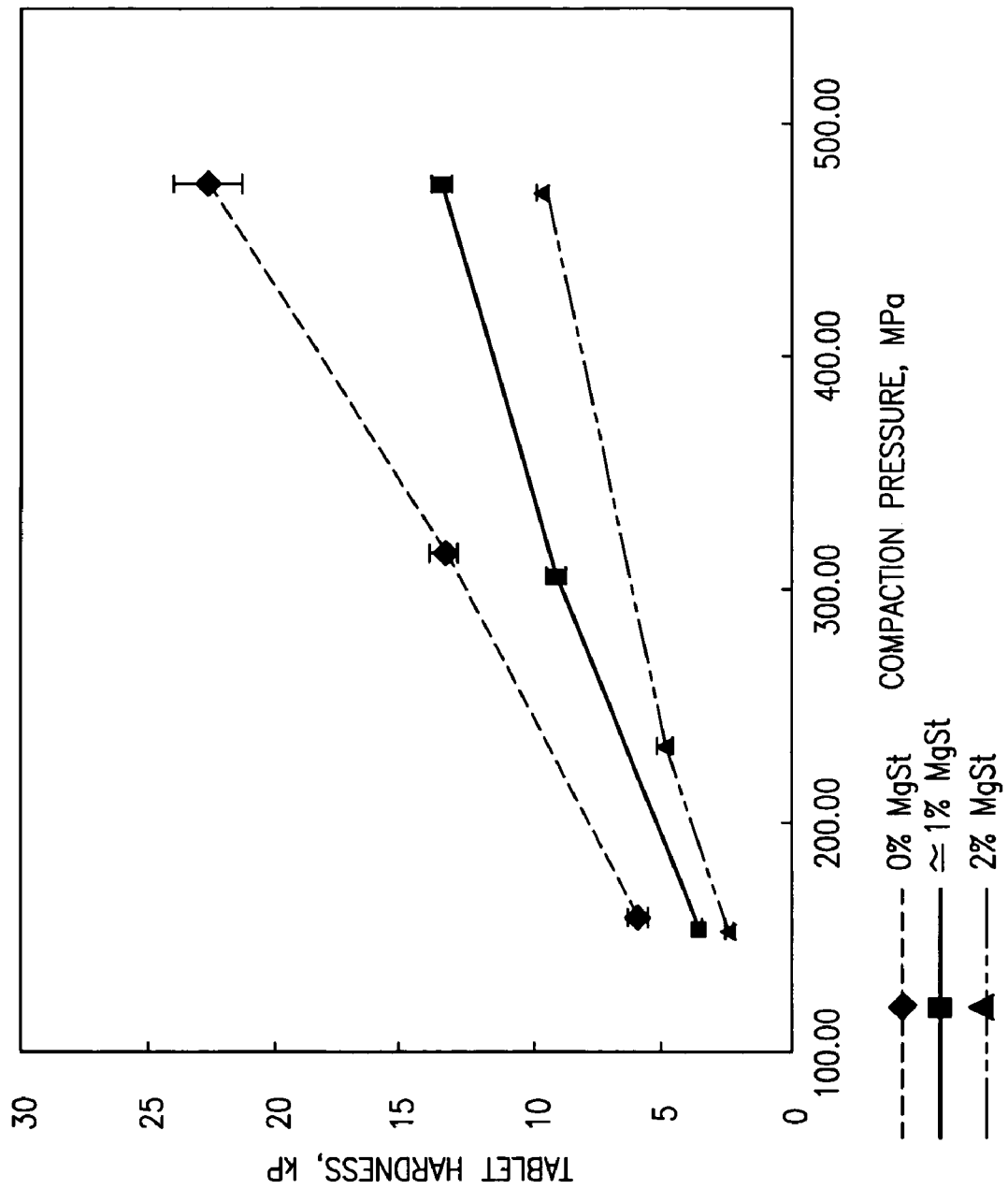
FIGS. 12 and 13 are charts showing relationships between the shear applied to a powder sample and the compactability of tablets formed.
Figure 13:
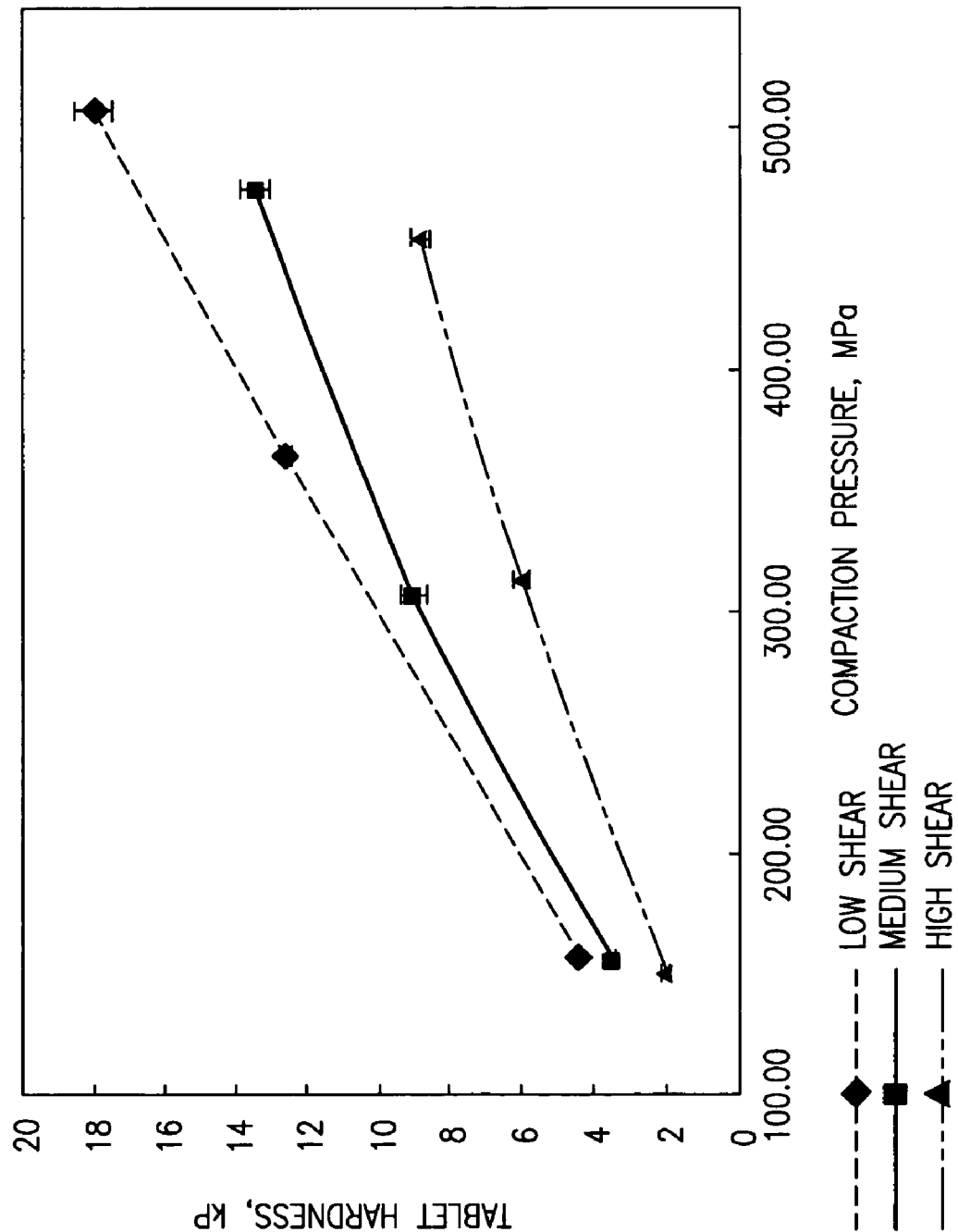

With reference to FIGS. 12 and 13, it was observed that tablet hardness is consistently and reproducibly affected by the amount of total shear imposed on the powder sample. FIGS. 12 and 13 demonstrate that the hardness of tablets formed from a powder sample not only depends on the MgSt concentration, but also depends on the level (i.e., amount) of shear applied to the powder sample. Samples with varying lubricant concentrations were taken from the shear application system after applying six thousand units of a substantially uniform level of shear at a uniform rate of ($100\ s^{-1}$), and compressing the powder sample into a Presster simulating a Fette PT 3090 61 station press at 60 RPM. The tablet crushing hardness was determined in a Schleuniger hardness tester. Higher lubricant concentrations showed a decrease in tablet hardness.

Figure 14:
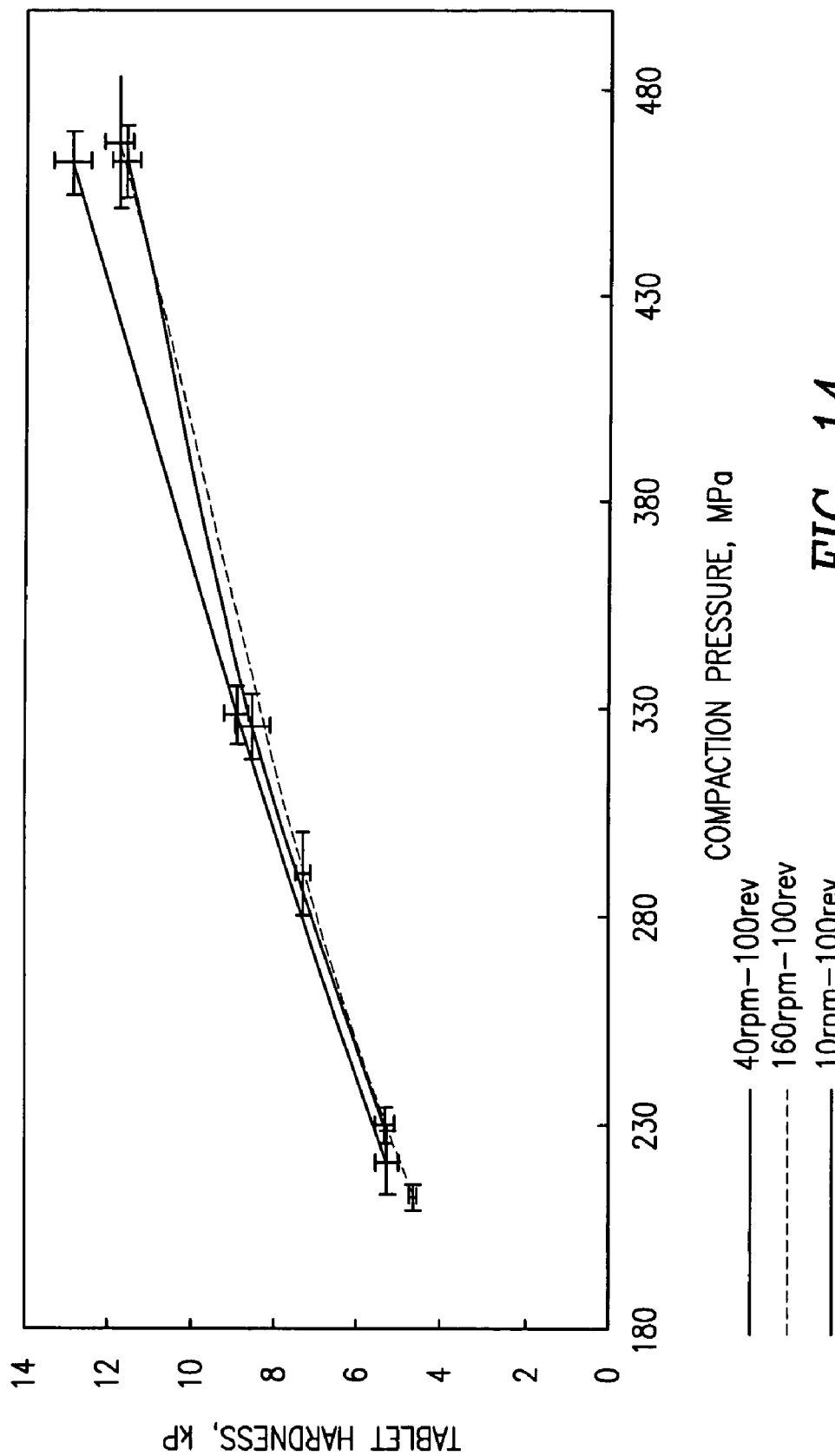
FIG. 14 is a chart showing a compactibility profile at different shear rates.

FIG. 12 shows the results for three powder samples, each having varying levels of MgSt sheared at the same rate and having the same total shear. As shown, tablet hardness decreases as the MgSt concentration is increased from 0% to 2%. As shown in FIG. 13, the effect of total shear on tablet hardness is studied by shearing three samples of identical composition (1% MgSt) at low (e.g., 3000 units), medium (e.g., 6000 units) and high (e.g., 7350 units) total shear. The results show a decrease in hardness as the total shear is increased. A simulated Fetter PT3090 61 press station was rotated at 60 RPM to obtain the results of FIG. 13. Referring to FIG. 14, the effect of different shear rates is shown on the relationship between compaction pressure and tablet hardness.

The test results shown in FIGS. 9-13 and discussed above in connection therewith demonstrate that the shear application system of the present invention can be used to create baseline values for shear having a low variance, and can be further used to increase/decrease the baseline values to obtain a test value for comparison and evaluation therewith. This facilitates the systematic study of the effects of shear on powder sample properties, such as particle size, particle shape, bulk density, flow properties, level of cohesion, etc., as well as the properties of tables formed therefrom, such as hardness, dissolution, friability, weight variability, etc. The shear application system may be constructed to handle any desired amount of powder and can be used as a formulation tool to optimize the amount of additives used in a given product. The shear application system may also be used as a process development tool to determine the optimum shear rate and total shear to apply to a powder sample for a given product thereof. The shear application system can also be used to optimize the granulation process. Results obtained from the shear application system can be correlated with additional results obtained in commercial blenders and feed frames in order to determine optimum process parameters in commercial equipment.

It will be understood that the embodiments of the present invention described herein are merely exemplary and that a person skilled in the art may make many variations and modifications without departing from the spirit and scope of the invention. All such variations and modifications, including those discussed above, are intended to be included within the scope of the invention as defined in the appended claims.

What is claimed is:

1. A shear application system for applying substantially uniform amounts of shear to a powder sample, said shear application system comprising:
   a cylinder assembly, comprising:
      an inner cylinder having an external cylindrical surface;
      a housing having (i) an internal cylindrical surface concentric with said external cylindrical surface, said internal and external cylindrical surfaces forming an annular chamber therebetween, (ii) a cover, and (iii) a base, said housing configured to contain the powder sample within said annular chamber; and
      a plurality of projections extending from said external cylindrical surface and said internal cylindrical surface for imparting shear to the powder sample in said annular chamber, said projections extending from said external cylindrical surface forming a first set of gaps with said internal cylindrical surface, said first set of gaps having a first distance, said projections extending from said internal cylindrical surface forming a second set of gaps with said external cylindrical surface, said second set of gaps having a second distance substantially equal to said first distance, each one of said plurality of projections extending from said external cylindrical surface being spaced apart by a third distance from each one adjacent thereto of said plurality of projections extending from said internal cylindrical surface, said third distance being substantially equal to said first and second distances;

drive means mechanically connected to said inner cylinder for inducing rotation of said inner cylinder in a direction of rotation; and control means electrically connected to said drive means for control thereof;

wherein said projections extending from said external cylindrical surface have angled forward edges having leading edges facing in the direction of rotation.

2. The shear application system of claim 1, wherein said housing comprises:

an outer cylinder forming said internal cylindrical surface;

wherein said is cover positioned over said annular chamber; and wherein said is base positioned under said annular chamber.

3. The shear application system of claim 1, wherein said plurality of projections comprises:

an inner set of lugs, each one of said lugs of said inner set extending radially outward from said external cylindrical surface; and an outer set of lugs, each one of said lugs of said outer set extending radially inward from said internal cylindrical surface.

4. The shear application system of claim 3, wherein said internal cylindrical surface and said lugs of said inner set form said first set of gaps therebetween, and wherein said external cylindrical surface and said lugs of said outer set form said second set of gaps therebetween.

5. The shear application system of claim 4, wherein each gap formed by said first and second sets is substantially the same size as each other gap formed by said first and second sets.

6. The shear application system of claim 3, wherein said lugs of said inner set comprise a plurality of vertically-aligned inner lug subsets, and wherein said lugs of said outer set comprise a plurality of vertically-aligned outer lug subsets.

7. The shear application system of claim 6, wherein each one of said plurality of vertically-aligned inner lug subsets is substantially even-spaced from each other one of said plurality of vertically-aligned inner lug subsets adjacent thereto.

8. The shear application system of claim 7, wherein each one of said plurality of vertically-aligned outer lug subsets is substantially even-spaced from each other one of said plurality of vertically-aligned outer lug subsets adjacent thereto.

9. The shear application system of claim 3, wherein said lugs of said inner set comprise a plurality of horizontally-aligned inner lug subsets, and wherein said lugs of said outer set comprise a plurality of horizontally-aligned outer lug subsets.

10. The shear application system of claim 9, wherein each one of said plurality of horizontally-aligned inner lug subsets is substantially even-spaced from each other one of said plurality of horizontally-aligned inner lug subsets adjacent thereto.

11. The shear application system of claim 10, wherein each one of said plurality of horizontally-aligned outer lug subsets is substantially even-spaced from each other one of said plurality of horizontally-aligned outer lug subsets adjacent thereto.

12. The shear application system of claim 9, wherein said plurality of horizontally-aligned inner lug subsets are alternatively positioned with respect to said plurality of horizontally-aligned outer lug subsets.

13. The shear application system of claim 12, wherein each of said horizontally-aligned inner lug subsets is substantially evenly-spaced from each horizontally-aligned outer lug subset adjacent thereto.

14. The shear application system of claim 1, wherein said drive means comprises a drive motor.

15. The shear application system of claim 1, wherein said control means is operative to input a user selection of at least one of an angular velocity and an amount of time, and wherein said control means is operative to variably actuate said drive means in accordance with said user selection.

16. The shear application system of claim 15, wherein said control means comprises a computer system comprising an electronic processor, an at least temporary memory, an input device, an output device, and a display.

17. The shear application system of claim 1, comprising at least one sensor for sensing attributes associated with at least one of the powder sample and said cylinder assembly and for sending said attributes to said control means.

18. The shear application system of claim 17, wherein said attributes comprise at least one of angular velocity of said inner cylinder, angular momentum of said inner cylinder, and an amount of force required to rotate said inner cylinder at a desired angular velocity.

19. The shear application system of claim 1, wherein at least one of said plurality of projections is interchangeably removable.

20. A shear application system for applying substantially uniform amounts of shear to a powder sample, said shear application system comprising:

a cylinder assembly, comprising:

an inner cylinder having an external cylindrical surface;

a housing having (i) an internal cylindrical surface concentric with said external cylindrical surface, said internal and external cylindrical surfaces forming an annular chamber therebetween, (ii) a cover, and (iii) a base, said housing configured to contain the powder sample within said annular chamber; and a plurality of projections extending from said external cylindrical surface and said internal cylindrical surface for imparting shear to a powder sample in said annular chamber, said plurality of projections extending from said external cylindrical surface comprising a plurality of vertically-aligned inner projection subsets each separated from each other one of said vertically-aligned inner projection subsets adjacent thereto by a first distance, and said plurality of projections extending from said internal cylindrical surface comprising a plurality of vertically-aligned outer projection subsets each separated from each other one of said vertically-aligned outer projection subsets adjacent thereto by a second distance substantially equal to said first distance;

drive means mechanically connected to said inner cylinder for inducing rotation of said inner cylinder in a direction of rotation; and control means electrically connected to said drive means for control thereof;

wherein said projections extending from said external cylindrical surface have angled forward edges having leading edges facing in the direction of rotation.

21. A shear application system for applying substantially uniform amounts of shear to a powder sample, said shear application system comprising:

a cylinder assembly, comprising:

an inner cylinder having an external cylindrical surface;

a housing having (i) an internal cylindrical surface concentric with said external cylindrical surface, said internal and external cylindrical surfaces forming an annular chamber therebetween, (ii) a cover, and (iii) a base, said housing configured to contain the powder sample within said annular chamber; and a plurality of projections extending from said external cylindrical surface and said internal cylindrical surface for imparting shear to a powder sample in said annular chamber, said plurality of projections extending from said external cylindrical surface including projections forming a first matrix pattern, said plurality of projections extending from said internal cylindrical surface including projections forming a second matrix pattern, said first and second matrix patterns configured to be positioned in substantial alignment with each other at a plurality of locations along said annular chamber;

drive means mechanically connected to said inner cylinder for inducing rotation of said inner cylinder in a direction of rotation; and control means electrically connected to said drive means for control thereof;

wherein said projections extending from said external cylindrical surface have angled forward edges having leading edges facing in the direction of rotation.

* * * * *

UNITED STATES PATENT AND TRADEMARK OFFICE
CERTIFICATE OF CORRECTION

PATENT NO. : 7,571,871 B2  Page 1 of 1
APPLICATION NO. : 11/267039
DATED : August 11, 2009
INVENTOR(S) : Fernando J. Muzzio et al.

It is certified that error appears in the above-identified patent and that said Letters Patent is hereby corrected as shown below:

Column 5, line 39, the word "opposited" should be deleted and replaced with the word "opposite."

Column 9, line 18, the word "is" prior to the word "cover" should be deleted, and it should be inserted after the word "cover."

Column 9, line 20, the word "is" prior to the word "base" should be deleted, and it should be inserted after the word "base."

Signed and Sealed this

Sixteenth Day of March, 2010

David J. Kappos
*Director of the United States Patent and Trademark Office*